(12) United States Patent
Schneider et al.

(10) Patent No.: US 9,290,439 B2
(45) Date of Patent: Mar. 22, 2016

(54) PROCESS FOR PREPARING CINACALCET AND PHARMACEUTICALLY ACCEPTABLE SALTS THEREOF

(71) Applicant: Produits Chimiques Auxiliaires et de Synthese, Longjumeau (FR)

(72) Inventors: Jean-Marie Schneider, Magnanville (FR); Jonathan Madec, Chatou (FR); Sergio Kreimerman, Houdan (FR); Gerard Guillamot, Viroflay (FR)

(73) Assignee: Produits Chimiques Auxiliaires et de Synthese, Longjumeau (FR)

( * ) Notice: Subject to any disclaimer, the term of this patent is extended or adjusted under 35 U.S.C. 154(b) by 0 days.

(21) Appl. No.: 14/425,905

(22) PCT Filed: Sep. 9, 2013

(86) PCT No.: PCT/EP2013/068617
§ 371 (c)(1),
(2) Date: Mar. 4, 2015

(87) PCT Pub. No.: WO2014/037563
PCT Pub. Date: Mar. 13, 2014

(65) Prior Publication Data
US 2015/0246869 A1     Sep. 3, 2015

(30) Foreign Application Priority Data
Sep. 7, 2012   (FR) .................................... 12 58408

(51) Int. Cl.
| | | |
|---|---|---|
| C07C 209/68 | (2006.01) | |
| C07C 209/52 | (2006.01) | |
| C07C 211/30 | (2006.01) | |
| C07C 249/02 | (2006.01) | |
| C07F 9/40 | (2006.01) | |

(52) U.S. Cl.
CPC ............. *C07C 209/68* (2013.01); *C07C 209/52* (2013.01); *C07C 211/30* (2013.01); *C07C 249/02* (2013.01); *C07F 9/40* (2013.01); *C07F 9/4006* (2013.01); *C07F 9/4015* (2013.01)

(58) Field of Classification Search
None
See application file for complete search history.

(56) References Cited

U.S. PATENT DOCUMENTS

| | | | |
|---|---|---|---|
| 5,648,541 A | 7/1997 | VanWagenen et al. | |
| 6,211,244 B1 | 4/2001 | VanWagenen et al. | |
| 7,247,751 B2 | 7/2007 | Lifshitz-Liron et al. | |
| 7,250,533 B2 | 7/2007 | Lifshitz-Liron et al. | |
| 7,393,967 B2 | 7/2008 | Lifshitz-Liron | |
| 2009/0093652 A1 | 4/2009 | Rafilovich et al. | |

FOREIGN PATENT DOCUMENTS

| | | |
|---|---|---|
| EP | 1 883 618 | 2/2008 |
| WO | WO 2006/125026 | 11/2006 |
| WO | WO 2006/127933 | 11/2006 |
| WO | WO 2006/127941 | 11/2006 |
| WO | WO 2007/062147 | 5/2007 |
| WO | WO 2007/112280 | 10/2007 |
| WO | WO 2007/127445 | 11/2007 |
| WO | WO 2007/127449 | 11/2007 |
| WO | WO 2008/000423 | 1/2008 |
| WO | WO 2008/035212 | 3/2008 |
| WO | WO 2008/058235 | 5/2008 |
| WO | WO 2008/058236 | 5/2008 |
| WO | WO 2008/068625 | 6/2008 |
| WO | WO 2009/153814 | 12/2009 |
| WO | WO 2010/015935 | 2/2010 |
| WO | WO 2010/049293 | 5/2010 |
| WO | WO 2010/067204 | 6/2010 |
| WO | WO 2010/103531 | 9/2010 |
| WO | WO 2010/128388 | 11/2010 |
| WO | WO 2011/050499 | 5/2011 |

OTHER PUBLICATIONS

Portnoy et al. (Tetrahedron Letters, 1971, 18, 1401).*
Whitesell et al. (Tetrahedron Letters, 1984, 25(20), 2119).*

* cited by examiner

*Primary Examiner* — Sudhakar Katakam
*Assistant Examiner* — Jennifer C Sawyer
(74) *Attorney, Agent, or Firm* — Buchanan Ingersoll & Rooney PC

(57) ABSTRACT

The present patent application relates to a process for preparing, cinacalcet or a pharmaceutically acceptable salt thereof, which comprises reacting 3-trifluoromethylbenzaldehyde having the following formula (II) with the phosphorus-comprising derivative having the following formula (III) in which $R_1$ and $R_2$, which may be identical or different, are each a ($C_1$-$C_6$)alkyl group. The present invention also relates to the phosphorus-comprising derivative having the formula (III), to the use thereof and to the process for preparing same. The present invention also relates to the phosphate salt of cinacalcet and to uses thereof.

12 Claims, 1 Drawing Sheet

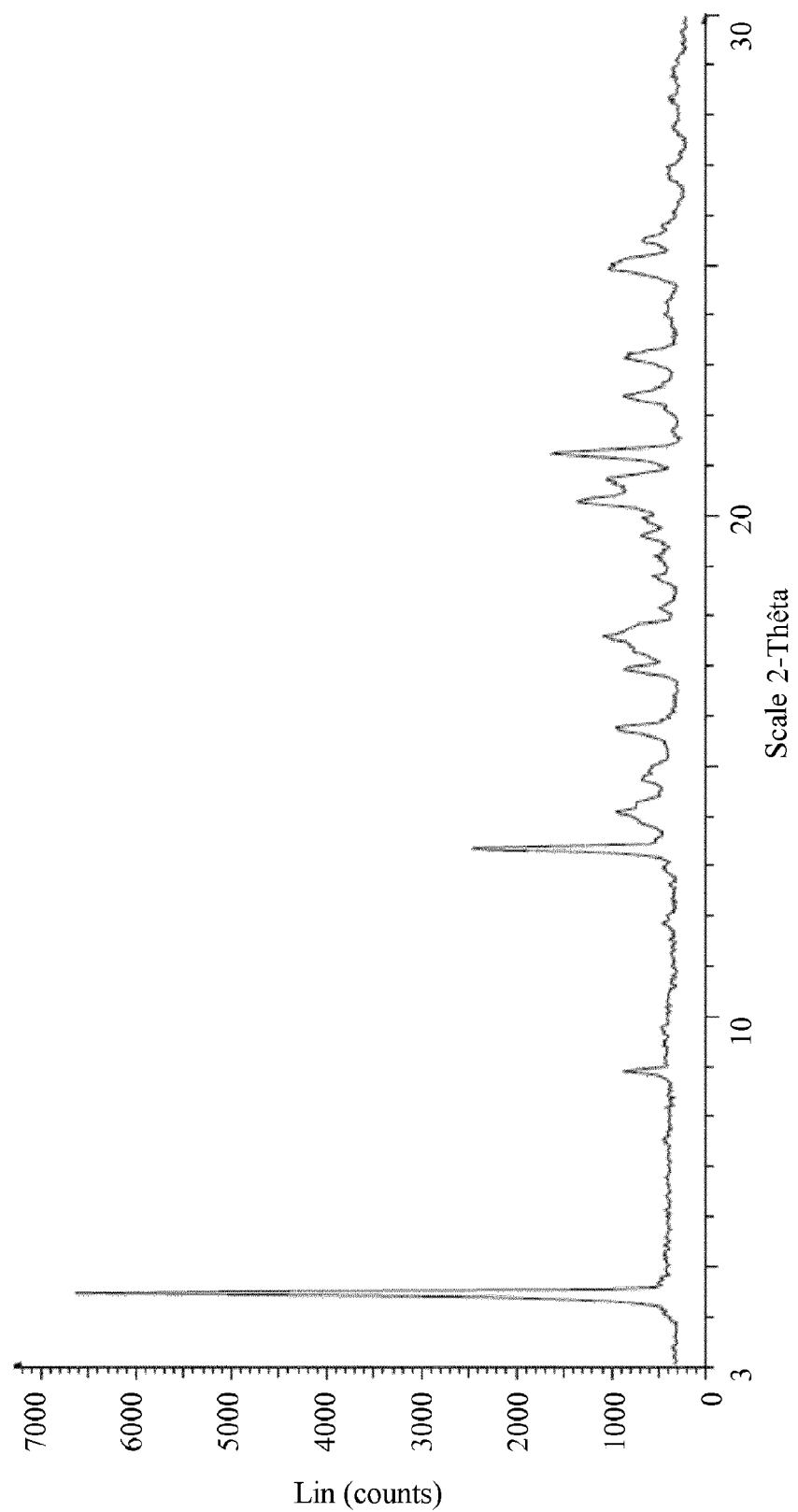

PROCESS FOR PREPARING CINACALCET AND PHARMACEUTICALLY ACCEPTABLE SALTS THEREOF

CROSS-REFERENCE TO RELATED APPLICATIONS

This application is a U.S. National Stage Application pursuant to 35 U.S.C. § 371 of International Patent Application PCT/EP2013/068617, filed on Sep. 9, 2013, and published as WO2014/037563 on Mar. 13, 2014, which claims priority to French Patent Application 1258408, filed on Sep. 7, 2012, all of which are incorporated herein by reference in their entireties for all purposes.

The present invention relates to a process for preparing cinacalcet ((R)-α-methyl-N-[3-[3-(trifluoromethyl)phenyl]-propyl]-1-naphthalenemethanamine) or one of the pharmaceutically acceptable salts thereof which makes particular use of diethyl ((R)-1-(1-naphthyl)ethylamino)vinylphosphonate as synthesis intermediate.

Cinacalcet is a calcimimetic active ingredient used in the treatment of hyperparathyroidism and is marketed in particular under the preparatory name Sensipar®.

Cinacalcet was described for the first time in 2006 in patent U.S. Pat. No. 6,211,244. Although a process for the preparation of cinacalcet is not described in this patent, similar compounds have been prepared by reaction between an amine and an aldehyde followed by reduction of the obtained imine in the presence of a cyanoborohydride.

Methods for preparing cinacalcet, analogue compounds and the pharmaceutically acceptable salts thereof have been described in patents U.S. Pat. No. 6,211,244, U.S. Pat. Nos. 7,250,533, 5,648,541, 7,247,751, 7,393,967, WO 06/125026, WO 06/127933, WO 06/127941, WO 07/062147, WO 07/112280, WO 07/127445, WO 07/127449, WO 08/058235, WO 08/000423, WO 08/035212, WO 08/058236, WO 08/06862, WO 2009153814, WO 2010067204, WO 2010015935, WO 2010049293, WO 2010103531, WO 2010128388, WO 2011050499.

WO 2009/153814 describes a process for preparing cinacalcet in accordance with the following reaction scheme:

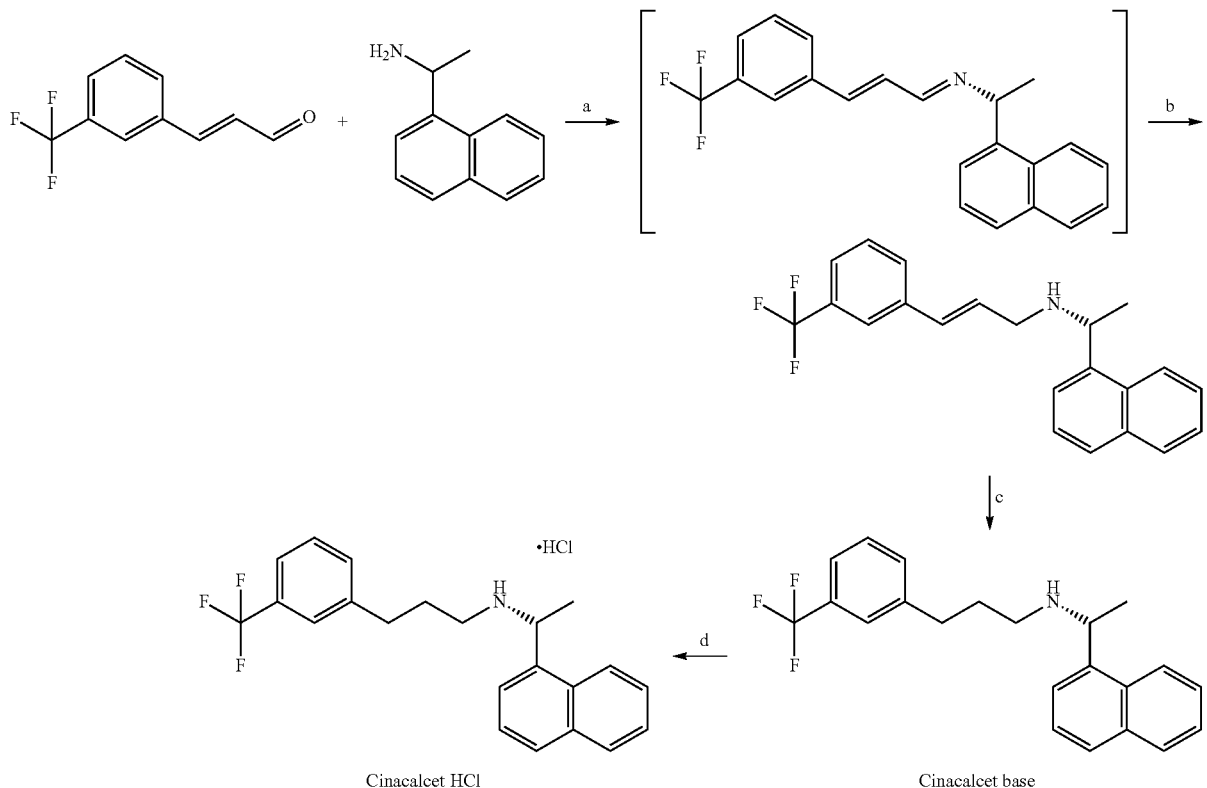

In this process, an unsaturated imine prepared from (R)-(+)-1-(1-naphthyl)ethylamine and 3-[3-(trifluoromethyl)phenyl]propenaldehyde, is converted to unsaturated cinacalcet in free from, which is then reduced by hydrogenation catalysed by palladium and the cinacalcet in free from is converted to cinacalcet hydrochloride with gaseous hydrochloric acid.

WO 2010/015935 describes another process for preparing cinacalcet in accordance with the following reaction scheme:

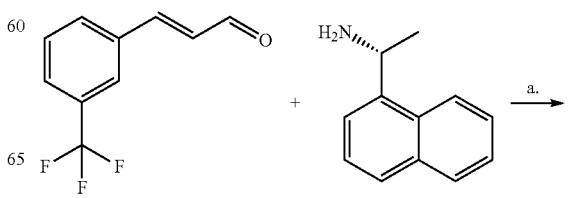

-continued

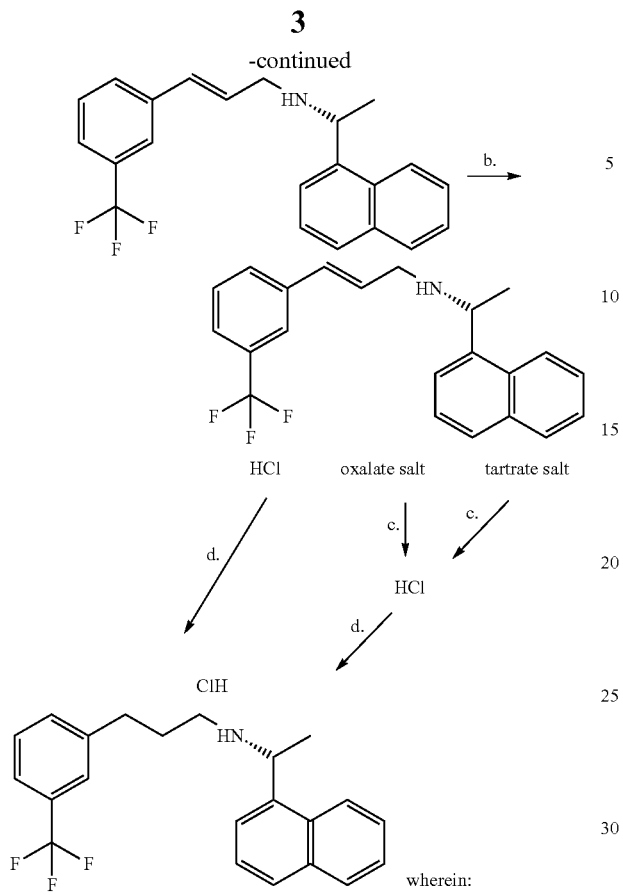

a. NaBH₄, methanol, b. HCl, acetonitrile/oxalic acid, acetonitrile/di-p-toluoyl-L-tartaric acid, methanol, c. (1) NaOH, water (2) HCl, acetonitrile, d. (1) Na₂CO₃, water, EtOAc (2) Pd(OH)₂, H₂ (3) NaHCO₃, di-tert-butyl dicarbonate, water, tetrahydrofuran (4) HCl, methanol.

The synthesis processes described in WO 2009/153814 and WO 2010/015935 have the drawbacks of using borohydrides which are toxic, and of requiring complicated reaction sequences to purify the cinacalcet.

In addition, most of these processes require the use of complex intermediates and of reagents which are not commercially available and must be previously synthesised. These processes are therefore not adapted for industrial application.

There is therefore a true need for the development of a novel route for synthesising cinacalcet which does not have the disadvantages of prior art methods.

The inventors have consequently developed a novel process for synthesising cinacalcet allowing for shorter synthesis and which is hence more economical and gives better performance.

The present invention therefore concerns a process for preparing cinacalcet of following formula (I):

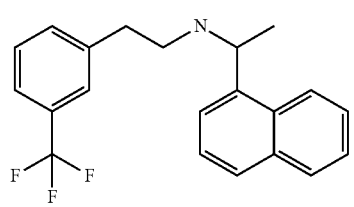

(I)

or one of the pharmaceutically acceptable salts thereof, comprising the reaction of 3-(trifluoromethyl)benzaldehyde of following formula (II):

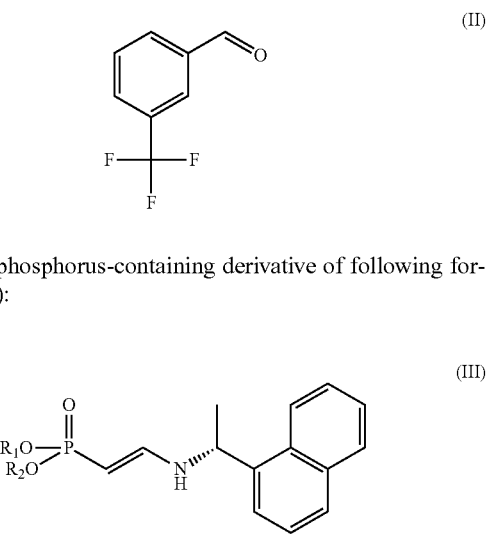

(II)

with the phosphorus-containing derivative of following formula (III):

(III)

where $R_1$ and $R_2$, the same or different, preferably the same, each represent a $(C_1\text{-}C_6)$alkyl group, e.g. an ethyl group.

In the present invention by <<pharmaceutically acceptable>> is meant that which is useful for the preparation of a pharmaceutical composition and is generally safe, non-toxic and neither biologically nor otherwise undesirable and which is acceptable for veterinary use as well as in human pharmaceutics.

By "pharmaceutically acceptable salts" of a compound is meant salts which are pharmaceutically acceptable as defined herein and which have the desired pharmacological action of the parent compound. Such salts comprise:

(1) pharmaceutically acceptable acid addition salts formed with pharmaceutically acceptable inorganic acids such as hydrochloric acid, hydrobromic acid, sulfuric acid, nitric acid, phosphoric acid and the like; or formed with pharmaceutically acceptable organic acids such as acetic acid, benzenesulfonic acid, benzoic acid, camphorsulfonic acid, citric acid, ethane-sulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalenesulfonic acid, propionic acid, salicylic acid, succinic acid, dibenzoyl-L-tartaric acid, tartaric acid, p-toluenesulfonic acid, trimethylacetic acid, trifluoroacetic acid and the like; or (2) the addition salts of pharmaceutically acceptable bases formed when an acid proton contained in the parent compound is either replaced by a metal ion e.g. an alkaline metal ion, an alkaline-earth metal ion or aluminium ion; or coordinated with a pharmaceutically acceptable organic or inorganic base. Acceptable organic bases include diethanolamine, ethanolamine, N-methylglucamine, triethanolamine, tromethamine and the like. Acceptable inorganic bases include aluminium hydroxide, calcium hydroxide, potassium hydroxide, sodium carbonate and sodium hydroxide.

Advantageously, it is an acid addition salt such as a hydrochloride or phosphate.

By "$(C_1\text{-}C_6)$alkyl" group in the meaning of the present invention is meant a linear or branched, saturated hydrocarbon chain having 1 to 6, preferably 1 to 4 carbon atoms. As examples mention can be made of the following groups: methyl, ethyl, propyl, isopropyl, butyl, isobutyl, sec-butyl, tert-butyl, pentyl or hexyl.

By "alkaline metal alkoxide" in the meaning of the present invention is meant a compound of formula AlkOM where M is an alkaline metal such as sodium, potassium or lithium, and preferably sodium or potassium, and Alk is a ($C_1$-$C_6$)alkyl group such as defined above. In particular it may be potassium or sodium tert-butoxide.

The reaction between the formula (II) and (III) compounds is advantageously performed in the presence of a base. The base can be selected from among sodium hydride, an alkaline metal alkoxide (e.g. potassium or sodium tert-butoxide), 2,2,6,6-lithium tetramethylpiperidide (LiTMP), lithium or potassium hexamethyldisilazide (LiHMDS or KHMDS), lithium diisopropylamide (LDA) or 1,8-diazabicyclo[5.4.0]undec-7-ene (DBU). The preferred base is sodium hydride.

The reaction between the formula (II) and (III) compounds can be conducted in a solvent. Preferably, the reaction is conducted in a polar aprotic solvent such as dimethylformamide (DMF), dimethylsulfoxide (DMSO), and ether solvents.

Advantageously, the solvent is an ether solvent such as tetrahydrofuran (THF), 2-methyl-tetrahydrofuran (MeTHF) or dimethyl ether (DME).

The ratio between the molar quantity of formula (II) aldehyde and the molar quantity of formula (III) phosphorus-containing derivative is advantageously between 0.9:1 and 1:0.9, in particular between 0.95:1 and 1:0.95, and is preferably about 1:1 (equimolar quantities of compounds (II) and (III)).

The reaction between the formula (II) and (III) compounds allows the enamine of following formula (IV) to be obtained:

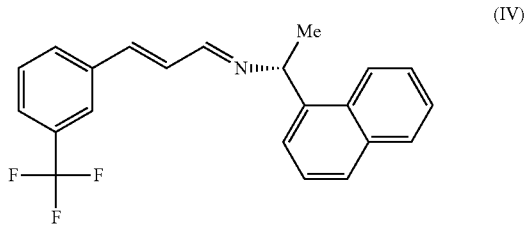 [SMILES: C[C@@H](/N=C/C=C/c1cccc(C(F)(F)F)c1)c1cccc2ccccc12]

(IV)

which can then be hydrogenated to give the cinacalcet of formula (I), this optionally being converted to a pharmaceutically acceptable salt.

The reduction of the formula (IV) compound can be conducted in a hydrogen atmosphere in the presence of a hydrogenation catalyst in particular a metal-based catalyst. For example, the metal may be palladium, nickel or rhodium.

According to one preferred embodiment, reduction is conducted with palladium on carbon (Pd/C) under a hydrogen atmosphere.

Reduction can be carried out in a solvent. Amongst suitable solvents, esters are cited such as a ($C_1$-$C_6$)alkyl acetates, in particular ethyl acetate, ($C_1$-$C_6$)-alkanols (i.e. a compound of formula R—OH where R=($C_1$-$C_6$)alkyl) such as ethanol or methanol, and the mixtures thereof. The preferred solvent is ethanol.

The conditions under which reduction can be performed, such as temperature, amount of metal, hydrogen pressure, reaction time and concentration can be determined by persons skilled in the art.

Advantageously, reduction is conducted at a temperature of between 20 and 25° C. in the presence of a catalytic amount of the hydrogenation catalyst, advantageously containing palladium such as Pd/C, and under a hydrogen pressure of 1 bar or higher, in particular between 1 and 5 bars. The amount of catalyst is advantageously less than 10 mole % relative to the quantity in moles of the formula (IV) compound to be hydrogenated.

The cinacalcet, after reduction of the formula (IV) enamine, can be isolated in its free form or in the form of a salt, using methods well known to skilled persons.

Preferably, the cinacalcet is obtained by precipitation in the form of an acid salt that is pharmaceutically acceptable, such as the phosphate salt or hydrochloride of cinacalcet. The cinacalcet salt thus precipitated can be then converted to another cinacalcet salt which is pharmaceutically acceptable.

The phosphorus-containing derivative of formula (III) such as defined previously can be obtained by reaction of the phosphonate derivative of following formula (V):

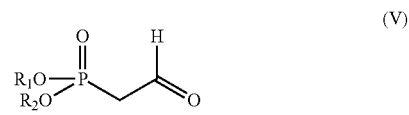

(V)

where $R_1$ and $R_2$ are as previously defined,
with (R)-(+)-1-(1-naphthyl)ethylamine of following formula (VI):

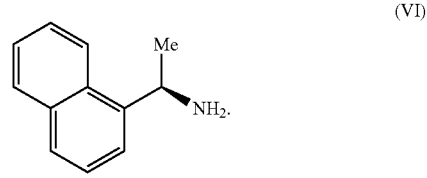 [SMILES: C[C@@H](N)c1cccc2ccccc12]

(VI)

This reaction can be conducted in an ether solvent such as tetrahydrofuran (THF), 2-methyltetrahydrofuran (MeTHF) or dimethyl ether (DME).

The ratio between the molar quantity of phosphonate derivative of formula (V) and the molar quantity of the amine (VI) is advantageously between 0.9:1 and 1:0.9, in particular between 0.95:1 and 1:0.95, and is preferably about 1:1 (equimolar quantities of compounds (V) and (VI)).

In one preferred embodiment, the reaction between the formula (V) compound and the formula (IV) compound can be carried out at a temperature of between 0 and 20° C., advantageously at about 10° C.

The phosphonate derivative of formula (V) as defined previously can be obtained by hydrolysis of the following formula (VII) compound:

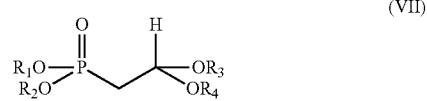

(VII)

where $R_1$ and $R_2$ are as defined previously and $R_3$ and $R_4$, the same or different, preferably the same, represent a ($C_1$-$C_6$) alkyl group, such as an ethyl group.

Preferably, the formula (VII) compound is diethyl 2,2-diethoxyethylphosphonate.

This hydrolysis reaction is advantageously conducted in an acid medium, in particular in the presence of oxalic acid or hydrochloric acid.

The hydrolysis of the formula (VII) compound and the reaction of the phosphorus-containing derivative of formula (V) with the amine of formula (VI) can be conducted in one and the same reactor without isolating the synthesis intermediates.

The process of the invention therefore allows the obtaining of cinacalcet or one of the pharmaceutically acceptable salts thereof in accordance with the following reaction scheme:

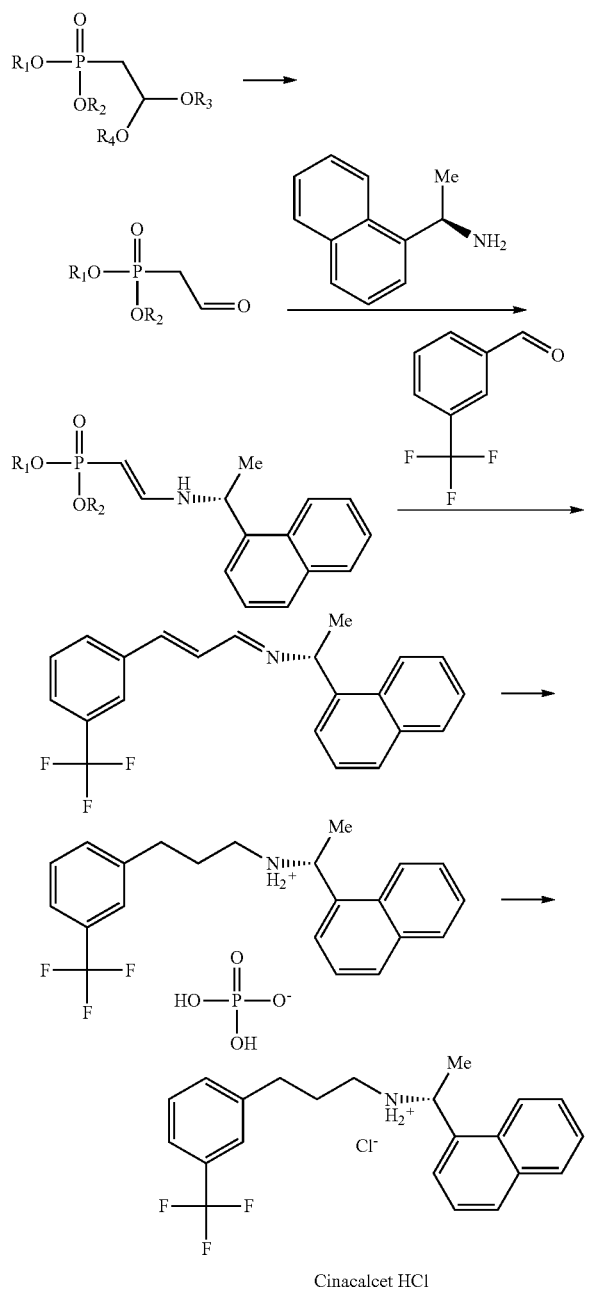

where $R_1$, $R_2$, $R_3$ and $R_4$ are as previously defined.

This process has the advantage of being able to be performed in a few steps, using nontoxic reagents that are low cost and easily commercially available.

The present invention also concerns (R)-(+)-1(1-naphthyl-ethylamino-vinyl-dialkyl-phosphonate of formula (III)

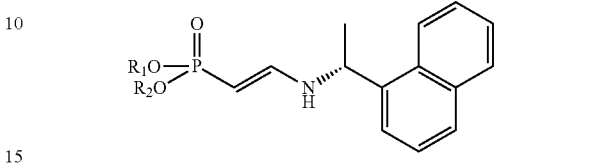

where $R_1$ and $R_2$ are as previously defined.

The present invention also concerns the use of a phosphorus-containing derivative of formula (III) as previously defined as synthesis intermediate in a process for preparing cinacalcet of formula (I) as defined previously or one of the pharmaceutically acceptable salts thereof, in particular cinacalcet hydrochloride.

The present invention also concerns a process for preparing the phosphorus-containing derivative of formula (III) as previously defined, comprising the reaction of the phosphonate derivative of following formula (V):

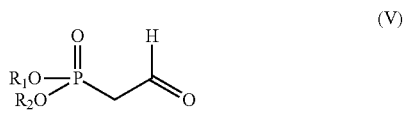

where $R_1$ and $R_2$ are as previously defined,
with (R)-(+)-1-(1-naphthyl)ethylamine of following formula (VI):

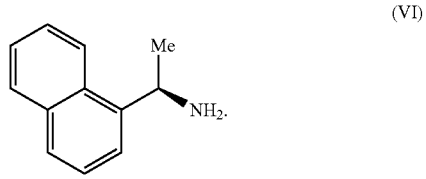 [SMILES: C[C@@H](N)c1cccc2ccccc12]

This reaction can be performed in an ether solvent such as tetrahydrofuran (THF), 2-methyltetrahydrofuran (MeTHF) or dimethyl ether (DME).

The ratio between the molar quantity of phosphonate derivative of formula (V) and the molar quantity of the amine (VI) is advantageously between 0.9:1 and 1:0.9, in particular between 0.95:1 and 1:0.95, and is preferably about 1:1 (equimolar quantities of compounds (V) and (VI)).

In one preferred embodiment, the reaction between the formula (V) compound and the formula (VI) compound can be conducted at a temperature of between 0 and 20° C., advantageously at about 10° C.

The phosphonate derivative of formula (V) as defined above can be obtained by hydrolysis of the compound of following formula (VII):

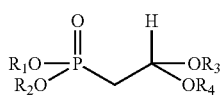
(VII)

where $R_1$ and $R_2$ are as previously defined and $R_3$ and $R_4$, the same or different, preferably the same, represent a ($C_1$-$C_6$) alkyl group e.g. an ethyl group.

Preferably the formula (VII) compound is diethyl 2,2-diethoxyethylphosphonate.

This hydrolysis reaction is advantageously performed in an acid medium, in particular in the presence of oxalic acid or hydrochloric acid.

The hydrolysis of the formula (VII) compound and the reaction of the phosphonate derivative of formula (V) with the amine of formula (VI) can be carried out in one and the same reactor without isolating the synthesis intermediates.

The invention also concerns a process for obtaining and/or purifying a crystalline form of a pharmaceutically acceptable salt of cinacalcet, advantageously from the cinacalcet obtained with the process for preparing cinacalcet according to the invention detailed in the foregoing, in particular a process for obtaining the phosphate salt of cinacalcet or the hydrochloride of cinacalcet.

In a first embodiment, the crystalline form of the pharmaceutically acceptable salt of cinacalcet is obtained by neutralising a cinacalcet salt followed by the addition of a pharmaceutically acceptable acid. According to this first embodiment, the cinacalcet hydrochloride can be prepared from the phosphate salt of cinacalcet.

In a second embodiment, the crystalline form of the pharmaceutically acceptable salt of cinacalcet is obtained by recrystallizing a pharmaceutically acceptable salt of cinacalcet, such as the hydrochloride of cinacalcet.

In a third embodiment, the crystalline form of the pharmaceutically acceptable salt of cinacalcet is obtained by the addition of a pharmaceutically acceptable acid to cinacalcet in the form of a free base and recrystallization of the pharmaceutically acceptable salt of cinacalcet obtained, such as the hydrochloride of cinacalcet.

The present invention therefore concerns a process for preparing cinacalcet hydrochloride, comprising the following successive steps:
  (a) neutralising a phosphate salt of cinacalcet to give cinacalcet in the form of a free base; and
  (b) reacting the cinacalcet in the form of a free base as obtained after previous step (a) with hydrochloric acid, optionally in gaseous form (also called hydrogen chloride) to give cinacalcet hydrochloride.

With said process it is possible to obtain cinacalcet hydrochloride in purified form. The choice of the phosphate salt in this process is important since the use of other salts does not allow the hydrochloride of cinacalcet to be obtained with such high degree of purity. Also, the direct conversion of cinacalcet in free base form to cinacalcet hydrochloride leads to a product which must be recrystallized several times to obtain an acceptable degree of purity.

Step (a):
The neutralisation step is advantageously conducted in ethyl acetate as solvent.

A base such as sodium hydroxide, in particular in an aqueous solution, can be used to release cinacalcet in free base form from its phosphate salt.

Neutralisation can therefore be carried out in a two-phase mixture comprising an organic solvent such as ethyl acetate and an aqueous solution containing a base such as an aqueous solution of sodium hydroxide.

Once the cinacalcet is in free base form, the reaction mixture can be washed with water, preferably demineralised water, to remove all the mineral salts formed during this step.

If necessary, the amount of solvent used at this step, and more particularly of ethyl acetate, can be adjusted before performing following step b) either by adding solvent, or by distilling a portion thereof to reduce the volume. The solvent could also be fully evaporated and be replaced by another solvent. Advantageously, one portion of the solvent is distilled before proceeding with step b) in the same solvent which is preferably ethyl acetate.

Step (b):
This step can advantageously be conducted in ethyl acetate as solvent in which the cinacalcet in free base form is solubilised.

Hydrochloric acid in gaseous form or optionally in solution in ethyl acetate is added to the reaction mixture to form cinacalcet hydrochloride.

Once the cinacalcet hydrochloride is formed, it can be crystallized by adding an anti-solvent and/or by cooling the reaction mixture to a temperature of 30° C. or lower, preferably between 0 and 30° C., and in particular at a temperature of about 0° C.

By "anti-solvent" in the meaning of the present invention is meant a solvent in which the cinacalcet hydrochloride is not soluble i.e. its solubility in the said solvent is 1 g/L or lower. In particular it may be heptane.

The cinacalcet hydrochloride can thus be obtained in crystalline and purified form.

The crystalline form of cinacalcet hydrochloride obtained is particularly in crystalline form I as described in patent application EP 1 883 618, which is characterized by the following peaks obtained by X-ray powder diffraction: 13.9; 19.0; 21.3 and 25.5±0.2° 2θ.

The process for preparing cinacalcet hydrochloride may therefore comprise the following successive steps:
  (i) solubilising a phosphate salt of cinacalcet in ethyl acetate;
  (ii) adding a base such as sodium hydroxide, in particular in aqueous solution, to form cinacalcet in the form of a free base;
  (iii) washing the reaction medium with water, preferably demineralised water;
  (iv) optionally distilling a portion of the solvent;
  (v) adding hydrochloric acid, in particular in gaseous form or optionally in solution in ethyl acetate, to form cinacalcet hydrochloride;
  (vi) adding heptane;
  (vii) cooling the reaction mixture to a temperature of 30° C. or lower, preferably between 0 and 30° C., in particular at a temperature of about 0° C.; and
  (viii) recovering the crystallized cinacalcet hydrochloride thus formed, in particular by filtration.

The present invention also concerns the phosphate salt of cinacalcet.

This phosphate salt of cinacalcet may be in polymorphous form, characterized by the following main peaks obtained by X-ray powder diffraction:

| d (Å) value | Relative intensity (%) |
|---|---|
| 19.86 | 100 |
| 9.95 | 12.9 |

-continued

| d (Å) value | Relative intensity (%) |
|---|---|
| 6.62 | 36.7 |
| 6.29 | 14.1 |
| 6.02 | 10.8 |
| 5.62 | 15.4 |
| 5.24 | 12.8 |
| 5.04 | 16.0 |
| 4.87 | 7.2 |
| 4.72 | 8.4 |
| 4.53 | 10.1 |
| 4.37 | 20.1 |
| 4.29 | 15.5 |
| 4.18 | 24.3 |
| 3.97 | 12.9 |
| 3.84 | 13.1 |
| 3.56 | 14.8 |
| 3.49 | 10.2 |

The present invention also concerns the phosphate salt of cinacalcet as medicament, advantageously used in the treatment of secondary hyperparathyroidism in patients suffering from chronic kidney failure and hypercalcaemia in patients suffering from cancer of the parathyroid gland.

The present invention also concerns the use of a phosphate salt of cinacalcet to prepare a medicament particularly intended for the treatment of secondary hyperparathyroidism in patients suffering from chronic kidney failure and hypercalcaemia in patients suffering from cancer of the parathyroid gland.

The present invention also concerns a therapeutic treatment method, more particular in order to treat secondary hyperparathyroidism in patients suffering from chronic kidney failure and hypercalcaemia in patients suffering from cancer of the parathyroid gland, comprising the administration, to a person in need thereof, of a therapeutically efficient amount of cinacalcet phosphate salt.

The present invention also concerns a pharmaceutical composition comprising a cinacalcet phosphate salt and one or more pharmaceutically acceptable excipients. This pharmaceutical composition may be in any suitable dosage form corresponding to a suitable route of administration. Preference is given to the oral route in capsule or tablet form.

The present invention will be better understood in the light of the following non-limiting examples.

FIGURE

FIG. 1: Diagram of X-ray powder diffraction of the phosphate salt of (R)-(−)-α-methyl-N-[3-[3-trifluoromethylphenyl]propyl]-1-naphthalene-methanamine.

EXAMPLES

Cinacalcet hydrochloride was prepared in accordance with the process of the present invention as illustrated in the following scheme:

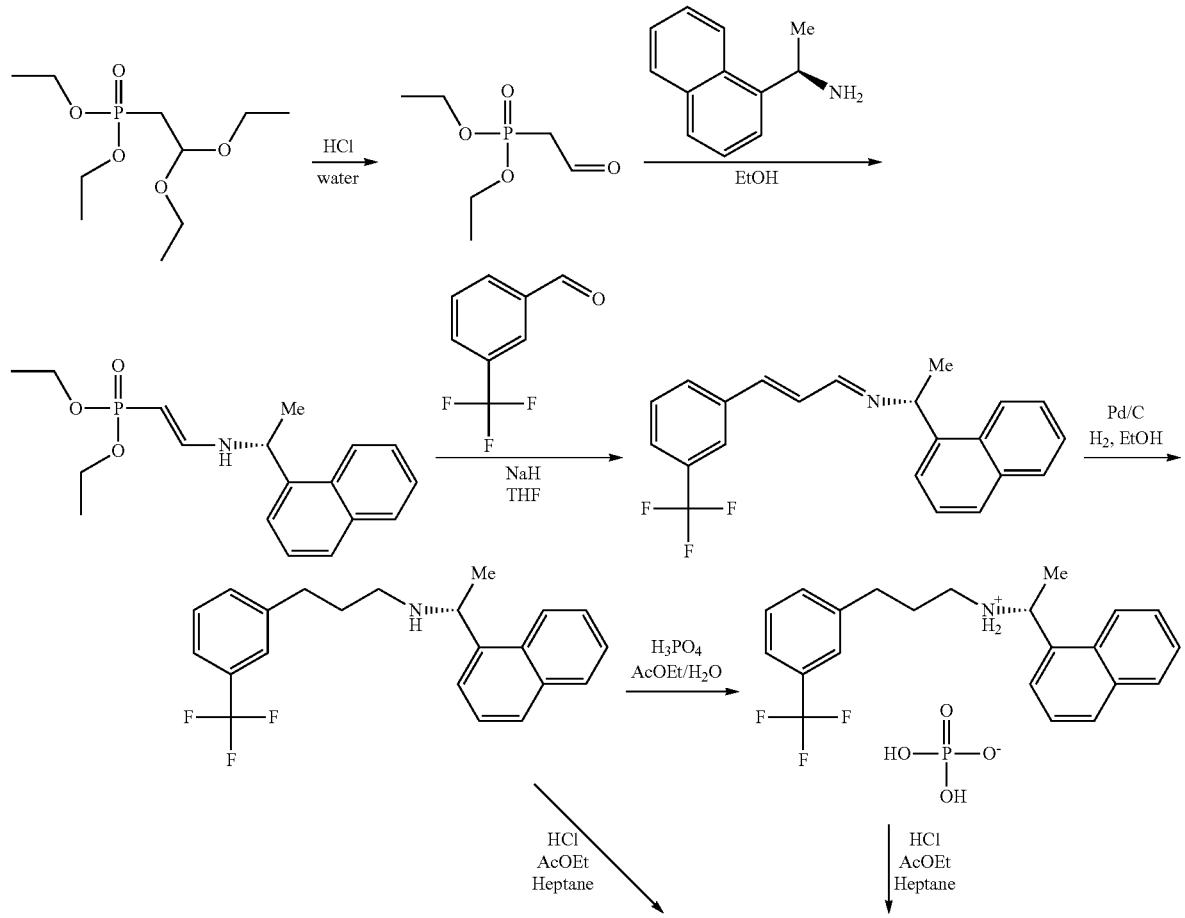

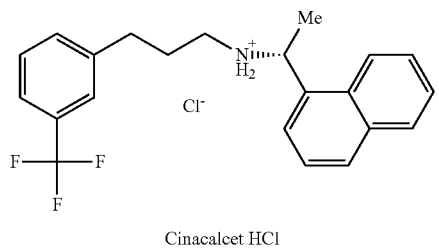

Cinacalcet HCl

Diethyl formylmethylphosphonate (Step 1)

A 2-litre, four-necked flask equipped with a mechanical stirrer, an addition funnel and a nitrogen inlet was charged with diethyl 2,2-diethoxyethylphosphonate (150 g) and water (300 mL), and a slight stream of nitrogen was continuously passed through the system. The resulting mixture was heated to 50° C. and hydrochloric acid (5.6 mL) was added. The mixture was then left under stirring for 4 hours after which water was added and the mixture concentrated under reduced pressure. Sodium chloride was added to the resulting mixture which was then extracted with 4 portions of ethyl acetate. The combined organic phases were distilled under reduced pressure.

Diethyl 2-((R)-1-(1-naphthyl)ethylamino)vinylphosphonate (Step 2)

A 1-litre, four-necked flask equipped with a mechanical stirrer, an addition funnel and a nitrogen inlet was charged with diethyl formylmethylphosphonate (100 g) and ethanol (500 mL). Under a nitrogen atmosphere, the resulting mixture was cooled to 10° C. and (R)-1-(1-naphthyl)ethylamine (85.6 g) was added under stirring. The mixture was left under stirring for an additional hour. The solvent was distilled from this mixture under reduced pressure. The resulting residue (180 g) was used in the next step without additional purification.

(R)-N-[3-[3-(Trifluoromethyl)phenyl]-2-propenylimino]-N-[1-(1-naphthyl)ethylamine] (Step 3)

A 1-litre, four-necked flask equipped with a mechanical stirrer, an addition funnel and a nitrogen inlet was charged with sodium hydride (10.72 g) (60% dispersion in oil) and tetrahydrofuran (150 mL). The system was placed under nitrogen and a solution of diethyl 2-((R)-1-(1-naphthyl)ethylamino)vinylphosphonate (74.3 g.) in anhydrous tetrahydrofuran (220 mL) was added. The mixture was left under stirring until completion of the reaction. A solution of 3-trifluoromethylbenzaldehyde (38.8 g) was added and the mixture stirred for an additional hour after which water was added to the mixture. The aqueous phase was extracted with methyl butyl ether. The combined organic phases were washed with water and distilled under reduced pressure. The resulting residue (78.8 g) was used in the next step without additional purification.

1$^{st}$ Alternative:

(R)-(−)-α-methyl-N-[3-[3-trifluoromethylphenyl]propyl]-1-naphthalenemethanamine hydrochloride (Step 4)

The palladium catalyst (5% Pd/C—2.1 g) was added to a solution of (R)-N-[3-[3-(trifluoromethyl)phenyl]-2-propenylimino]-N-[1-(1-naphthyl)ethylamine] (44.2 g) in ethanol (440 mL) at ambient temperature under $H_2$ pressure (3 bars). The mixture was stirred until completion of the reaction. The heterogeneous mixture was filtered and a 20% solution of hydrochloric acid in isopropanol (27.4 g) was added at ambient temperature. The mixture was evaporated to dryness under reduced pressure.

Ethyl acetate was added and the mixture stirred. Heptane was then added at ambient temperature and the mixture stirred. The solid obtained was filtered, washed and dried under reduced pressure to give 29.5 g of product (yield: 60%; purity: 95.0%).

The product was recrystallized a second time following the same procedure (treatment with ethyl acetate followed by heptane) to give the desired product with a yield of 80% and purity of 99.3%.

2$^{nd}$ Alternative:

Phosphate Salt of (R)-(−)-α-Methyl-N-[3-[3-trifluoromethylphenyl]propyl]-1-naphthalenemethanamine (Step 4)

In 1-litre hydrogenation apparatus equipped with a mechanical stirrer, the palladium catalyst (5% Pd/C—4.8 g) and a solution of (R)-N-[3-[3-(trifluoromethyl)phenyl]-2-propenylimino]-N-[1-(1-naphthyl)ethylamine] (82.2 g) in ethanol (500 mL) at ambient temperature and under $H_2$ pressure (3 bars) were left under stirring for 4 hours. When the reaction was completed the heterogeneous mixture was filtered. The solvent was distilled from the mixture under reduced pressure. Ethyl acetate was added. The solvents were distilled from the mixture under reduced pressure. Ethyl acetate and water were added at ambient temperature followed by phosphoric acid (85% wt/wt—19.3 mL) After seeding (1% wt/wt), the mixture was stirred for 2 additional hours at ambient temperature and cooled to 0° C. The mixture was stirred at 0° C. and the solid was filtered, washed with ethyl acetate and dried under reduced pressure to give 63.5 g of product (60%).

A 1-litre, four-necked flask equipped with a mechanical stirrer and a nitrogen inlet was charged with the phosphate salt of (R)-(−)-α-methyl-N-[3-[3-trifluoromethylphenyl]propyl]-1-naphthalenemethanamine (100.0 g), ethyl acetate (500 mL) and water (100 mL). The resulting suspension was heated to 70° C. and then cooled. The solid obtained was filtered, washed with ethyl acetate and dried under reduced pressure to give 95.0 g of product (95%).

The phosphate salt thus obtained was analysed under X-ray powder diffraction (XRPD) under the following conditions:
Siemens diffractometer D5000
Copper anticathode, voltage 10 kV, intensity 40 mA
θ-θ assembly, fixed sample
Ambient temperature
Measurement range: 3° to 30°

Incrementation beween each measurement: 0.04°

Measuring time pitch: 4 s

Fixed slits: 1.6 mm

No internal reference

Zero procedure with Siemens slits

Obtained experimental data processed using EVA software (v. 12.0)

The diagram of X-ray powder diffraction obtained is shown in FIG. 1. The main peaks obtained in this diagram are characterized in the Table below.

| Angle 2θ (°) | Value d (Å) | Intensity (counts) | Relative intensity (%) |
|---|---|---|---|
| 4.445 | 19.86 | 6655 | 100 |
| 8.880 | 9.95 | 856 | 12.9 |
| 13.356 | 6.62 | 2444 | 36.7 |
| 14.073 | 6.29 | 941 | 14.1 |
| 14.714 | 6.02 | 716 | 10.8 |
| 15.765 | 5.62 | 1026 | 15.4 |
| 16.918 | 5.24 | 851 | 12.8 |
| 17.596 | 5.04 | 1068 | 16.0 |
| 18.200 | 4.87 | 476 | 7.2 |
| 18.787 | 4.72 | 561 | 8.4 |
| 19.600 | 4.53 | 669 | 10.1 |
| 20.306 | 4.37 | 1338 | 20.1 |
| 20.699 | 4.29 | 1030 | 15.5 |
| 21.239 | 4.18 | 1619 | 24.3 |
| 22.393 | 3.97 | 857 | 12.9 |
| 23.166 | 3.84 | 871 | 13.1 |
| 25.024 | 3.56 | 986 | 14.8 |
| 25.508 | 3.49 | 680 | 10.2 |

(R)-(−)-α-methyl-N-[3-[3-trifluoromethylphenyl]propyl]-1-naphthalenemethanamine hydrochloride (Step 5)

A 1-litre, four-necked flask equipped with a mechanical stirrer, an addition funnel and nitrogen inlet was charged with the phosphate salt of (R)-(−)-α-methyl-N-[3-[3-trifluoromethylphenyl]propyl]-1-naphthalenemethanamine (92 g) and ethyl acetate (368 mL) at ambient temperature. The system was placed under nitrogen and a solution of sodium hydroxide (20% NaOH—68 mL) in water (278 mL) was added under stirring. The two-phase solution was left under stirring for 1 additional hour. The organic phase was recovered, washed with water, concentrated under reduced pressure and used in the remaining procedure. HCl gas (m g) was added to the solution under stirring and at ambient temperature but with temperature control to ensure that the temperature of the solution did not exceed 25° C. The solution was cooled to 10° C. and stirred for 30 minutes.

Heptane was then added and the mixture was stirred. The resulting suspension was stirred at 10° C. then cooled to 0° C. The solid obtained was filtered, washed with ethyl acetate/heptane mixture 50:50 v/v and dried under reduced pressure to give 75.6 g of the desired product (yield: 94%; purity: 99.9%).

The invention claimed is:

1. A process for preparing cinacalcet or one of the pharmaceutically acceptable salts thereof, comprising the reaction of 3-trifluoromethyl-benzaldehyde of following formula (II):

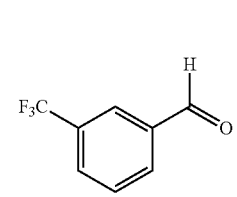

with the phosphorus-containing derivative of following formula (III):

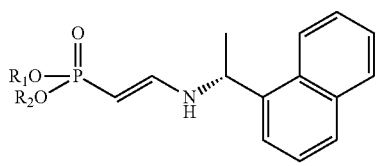

where $R_1$ and $R_2$, the same or different, each represent a $(C_1–C_6)$alkyl group.

2. The process according to claim 1, wherein $R_1$ and $R_2$ are the same.

3. The process according to claim 2, wherein $R_1$ and $R_2$ each are an ethyl group.

4. The process according to claim 1, wherein the reaction is conducted in the presence of a base.

5. The process according to claim 4, wherein the base is selected from the group consisting of sodium hydride, an alkaline metal alkoxide, lithium 2,2,6,6-tetramethylpiperidide (LiTMP), lithium or potassium hexamethyldisilazide (LiHMDS or KHMDS), lithium diisopropylamide (LDA), and 1,8-diazabicyclo[5.4.0]undec-7-ene (DBU).

6. The process according to claim 1, wherein the reaction is conducted in a solvent selected from among dimethylformamide (DMF), dimethylsulfoxide (DMSO), tetrahydrofuran (THF), 2-methyl-tetrahydrofuran (MeTHF), and dimethyl ether (DME).

7. The process according to claim 1, wherein the (II):(III) weight ratio is about 1:1.

8. The process according to claim 1, wherein the compound of following formula (IV):

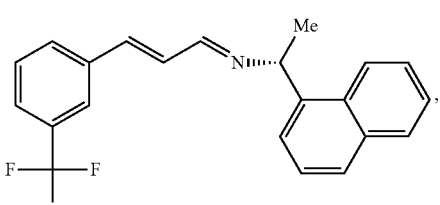

obtained by reaction of the compounds of formula (II) and (III), is hydrogenated to give cinacalcet, which is optionally converted to a pharmaceutically acceptable salt.

9. The process according to claim 8, wherein hydrogenation is performed under a hydrogen atmosphere in the presence of a hydrogenation catalyst.

10. The process according to claim 9, wherein the hydrogenation catalyst is palladium on carbon (Pd/C).

11. The process according to claim 9, wherein the hydrogenation reaction is conducted in ethanol or methanol as solvent.

12. The process according to claim 1, wherein the pharmaceutically acceptable salt of cinacalcet is the hydrochloride of cinacalcet or the phosphate salt of cinacalcet.

* * * * *